United States Patent [19]

Reinalda et al.

[11] Patent Number: 5,217,938

[45] Date of Patent: Jun. 8, 1993

[54] PROCESS FOR THE PREPARATION OF ZIRCONIA-BASED CATALYST

[75] Inventors: Donald Reinalda; Paul Blankenstein, both of Amsterdam, Netherlands

[73] Assignee: Shell Oil Company, Houston, Tex.

[21] Appl. No.: 871,791

[22] Filed: Apr. 21, 1992

[30] Foreign Application Priority Data

Apr. 23, 1991 [GB] United Kingdom ................. 9108656

[51] Int. Cl.$^5$ .......................... B01J 21/06; B01J 23/74
[52] U.S. Cl. .................... 502/325; 502/337; 502/338; 502/349
[58] Field of Search ............... 502/242, 325, 337, 338, 502/349; 423/608

[56] References Cited

U.S. PATENT DOCUMENTS 3,642,933  2/1972  Heckelsberg .................. 502/349 X
5,106,549  4/1992  Daamen et al. ....................... 264/56

FOREIGN PATENT DOCUMENTS 63-63788  3/1988  Japan .................................. 502/349

Primary Examiner—W. J. Shine

[57] ABSTRACT

A zirconia-based catalyst is prepared by mulling a mixture of a zirconia source and a solvent, which mixture has a solids content of from 20% by weight to 60% by weight, and extruding the mixture.

25 Claims, No Drawings

PROCESS FOR THE PREPARATION OF ZIRCONIA-BASED CATALYST

BACKGROUND OF THE INVENTION

1. Field of the Invention

The present invention relates to a process for the preparation of a zirconia-based catalyst by mulling a mixture of a zirconia source and a solvent, which mixture has a solids content of from about 20% to about 60% by weight, and extruding the mixture.

2. Description of the Prior Art

The preparation of catalysts comprising zirconium oxide/hydroxide carriers on which the catalytically active component cobalt has been deposited is disclosed in Japanese patent application No. JP 63063788. The process involves adding an alkali to an aqueous solution of a zirconium salt such as zirconium chloride or zirconium nitrate thereby producing a precipitate which is washed, filtered and dried or burned to produce the zirconium oxide/hydroxide carrier. Cobalt is deposited on the carrier by immersing the carrier in an aqueous solution of cobalt nitrate. The catalyst produced can be used to obtain a middle-cut hydrocarbon fraction from a gaseous mixture of carbon monoxide and hydrogen.

A number of disadvantages are associated with the process disclosed by JP 63063788. First of all, the precipitate produced is limited in its applications as a carrier for a catalyst. Furthermore, the number of steps needed to produce the catalyst or catalyst carrier make production on a commercial scale difficult.

It has now been found that the present proces provides a much simpler process for preparing a zirconia-based catalyst by means of extrusion. This process is also very suitable for use on a commercial scale.

SUMMARY OF THE INVENTION

The present invention provides a process for preparing a zirconia-based catalyst comprising mulling a mixture of a zirconia source and a solvent, which mixture has a solids content of from about 20% to about 60% by weight, followed by extruding the mixture. As prepared, this catalyst comprises a carrier consisting substantially or wholly of the zirconia source.

DESCRIPTION OF THE PREFERRED EMBODIMENTS

The present invention provides a process for the preparation of a zirconia-based catalyst. As used herein, the term "zirconia-based catalyst" includes any zirconia-based catalyst precursor which when utilized within the present process yields the same results as the use of a zirconia-based catalyst. This zirconia-based catalyst precursor can also be utilized as a catalyst support to add additional catalytically active components above and beyond those catalytically active components added to the zirconia-based catalyst.

The process of the present invention encompasses mulling a mixture of a zirconia source and a solvent and extruding the mixture. The mixture preferably has a solids content from about 20% by weight to about 60% by weight. As used herein, the term "zirconia source" includes zirconia and/or a zirconia precursor. The zirconia precursor utilized can be any zirconium compound including zirconium salts derived from organic acids or inorganic salts. Suitable salts derived from organic acids include, but are not limited to, zirconium acetate, zirconium propionate, and zirconium benzoate. Suitable inorganic salts include, but are not limited to, zirconium chloride, zirconium bromide, zirconium iodide, zirconium fluoride, zirconium nitrate, zirconium carbonate, zirconium sulphate, and zirconium chlorate. The preferred zirconia precursor, however, is zirconium hydroxide.

The mixture of the claimed process also includes an inert, liquid solvent selected from conventional solvents. These solvents include, but are not limited to, conventional solvents including: water; alcohols, such as methanol, ethanol, and propanol; ketones, such as acetone and methyl ethyl ketone; aldehydes, such as propanal and butanal; and aromatic solvents, such as toluene and benzene. In the preferred embodiment of the invention, water is used as the solvent.

The mixture may further comprise one or more other refractory oxide sources including refractory oxides and refractory oxide precursors. Suitable refractory oxides include, but are not limited to, silica, titania, alumina, or mixtures thereof with silica being the preferred refractory oxide. Suitable silicas include, but are not limited to, silica gel, precipitated silica and pyrogenic silica, with precipitated silica being the most preferred. The refractory oxide source can be present in an amount of up to about 100% by weight on the basis of the amount of zirconia present in the final product. When one or more other refractory oxide sources are included, it is preferred that an amount of refractory oxide ranging from about 5% by weight to about 50% by weight is present, and even more preferred is an amount ranging from about 5% by weight to about 25% by weight.

A volatile basic compound can also be included in the mixture in order to obtain strong extrudates. These components act as peptizing agents thereby stabilizing the zirconia source. Including these compounds in the mixture does not impair the final product since they are removed when the product is calcined.

The amount of basic compound included in the mixture should be sufficient to peptize the zirconia source. This amount can be determined by measuring the pH of the mixture. During mulling, the mixture should have sufficient basic compound to provide a pH in the range of from about 8.0 to about 11.5, preferably from about 9.0 to about 11.0.

The zirconia in the extrudate prepared by the process of the present invention can be used as a catalytically active component. The mixture from which the extrudate is formed can also contain sources of one or more additional catalytically active components or promoter elements of the catalytically active components chosen from Groups IB-VIIB and VIII of the Periodic Table of Elements, with the Group VIII elements being preferred. Sources containing iron, ruthenium, cobalt, rhenium, nickel, palladium, platinum, copper and zinc are especially preferred, with cobalt, iron and nickel being the more preferred, and cobalt being the most preferred. When sources containing promoter elements are utilized, they are preferably chosen from sources of elements of Group IVB of the Periodic Table of Elements, with titanium being the preferred promoter.

The source of the one or more additional catalytically active components or promoter elements of catalytically active components can be soluble or insoluble in the solvent, with sources which are insoluble being preferred. Typical sources include, but are not limited to: salts derived from organic acids, such as acetates, benzoates, and propionates; halides, such as chlorides, bromides, iodides, and fluorides; and other salts, such as nitrates, oxides, hydroxides, carbonates, and chlorates. Hydroxides are particularly suitable sources for the catalytically active components and promoters elements.

The basic compound chosen can function as both the source of one or more catalytically active components or promoter elements of the catalytically active component and as the basic compound in the mixture. In the alternative, the basic compound chosen can be added to one or more different sources having one or more catalytically active components or promoter elements of catalytically active components. The preferred basic compounds include ammonia-releasing compounds, ammonium compounds and organic amines, with the more preferred being organic amines such as ethanolamine and ammonium compounds such as ammonium carbonate. The most preferred basic compound is ammonium zirconium carbonate.

It is useful on occassion to add to this mixture during mulling a surface active agent or polyelectrolyte to improve the flux properties of the mixture during extrusion and to facilitate the cutting of the extruded product. This addition may also improve the formation of micropores in the calcined product thereby possibly enhancing the catalytic properties of the products produced. Suitable conventional surface active agents useful for this purpose include cationic, anionic, and nonionic surface active agents. The amount of surface active agent added typically ranges from about 0.5% by weight to about 8% by weight, preferably from about 1% by weight to about 5% by weight, based on the weight of the zirconia source present in the mixture.

In the process of the present invention, the mixture of the various ingredients utilized is mulled. While it is possible to add the ingredients of the mixture in any order, it is preferred to first combine and mull the zirconia source and the solvent. The basic compound, if included, should be added to the mixture after the zirconia source and solvent have been combined, together with any other refractory oxide sources. Combining the components in this order avoids the considerable uptake of the basic compound into the pores of the solid material thereby resulting in an improved extrudate since any basic compound confined within the pores of the solid material prevents full peptization and requires the addition of further basic compound to achieve satisfactory peptization. The uptake of the basic compound also causes extrudates with lower crush strengths.

Since mixtures having a high pH are more difficult to extrude than mixtures having a pH in the range from about 7.0 to about 9.0, the pH of the mixture of the present invention is preferentially reduced to a pH within this range after allowing sufficient time for the zirconia source to be peptized by the basic compound, but before extrusion. The pH can be reduced by adding an organic or inorganic acid. An organic acid selected from formic acid, acetic acid, propionic acid or butanoic acid is preferred, with acetic acid being the most preferred.

If catalytically active components or promoter elements are used, the source of the catalytically active components or promoter elements is added and the resulting mixture subjected to further mulling. As noted previously, a surface active agent can be added during the mulling, preferably just prior to a final period of mulling.

Typically, the mixture is mulled for a total period of from about 10 minutes to about 120 minutes, preferably from about 15 minutes to about 90 minutes. Any suitable, commercially available mulling apparatus can be used. During the mulling process, energy is input into the mixture by the mulling apparatus at a rate typically from about 0.05 Wh/min/kg to about 50 Wh/min/kg, preferably from about 0.5 Wh/min/kg to about 10 Wh/min/kg. The mulling process may be carried out at ambient pressure and over a broad range of temperatures, with the preferred temperature being from about 15° C. to about 50° C.

Once the mulling process has been completed, the resulting mixture is then extruded using any conventional, commercially available extruder. In particular, a screw-type extruder can be used to force the mixture through orifices in a suitable dieplate to yield extrudates of any shape known in the art. The process of the present invention is particularly suitable for forming trilobe extrudates having a nominal diameter of from about 0.5 millimeters to about 5 millimeters, preferably from about 1 millimeter to about 3 millimeters. The strands formed upon extrusion can be cut to any desired length.

After extrusion, the extrudates are dried, typically for up to about 5 hours, even more preferably from about 30 minutes to about 3 hours, at an elevated temperature of up to about 300° C. The extrudates are then preferably calcined for a period of up to about 5 hours, preferably from about 30 minutes to about 4 hours. Calcination is carried out at an elevated temperature of up to about 1000° C., preferably from about 325° C. to about 1000° C., more preferably from about 350° C. to about 800° C.

Once the extrudates are prepared and calcined, the source of one or more catalytically active components or promoter elements of the catalytically active components can be deposited on them. In cases in which a source of a catalytically active component or promoter element is included in the original mixture, additional sources of components or elements can be added to increase the loading of the extrudates.

The source of the catalytically active components or promoter elements can be deposited on the extrudate by any of the techniques known in the art. The deposition can be accomplished in either one or more steps with the order in which multiple sources of catalytically active components or promoter elements are deposited being largely a matter of choice and convenience. However, the preferred order is to first deposit the source of the promoter element on the extrudate followed by the source of one or more catalytically active components.

Impregnation is the preferred technique for deposition. When impregnation is utilized, the deposition can be effected by contacting the extrudate with the source of the desired catalytically active component or promoter element in the presence of a liquid. Suitable liquids for use in impregnation include both organic and inorganic liquids, with water being the preferred liquid. Suitable sources include both organic and inorganic compounds. Inorganic compounds are preferable, with nitrates being the most preferred inorganic compounds.

The additional catalytically active component is present in an amount of from about 1 part to about 100 parts by weight, preferably from about 10 parts to about 50 parts by weight, per 100 parts by weight of zirconia. The promoter, if present, can be present in an amount of from about 1 parts to about 60 parts by weight, preferably from about 2 parts to about 40 parts by weight, per 100 parts by weight of zirconia.

The extrudates are dried and calcined after each catalytically active component or promoter element of the catalytically active component is deposited. The final product can be applied in any process in which a zirconia-based catalyst can be used or is required. In particular, products of the process are advantageous when comprising catalytically active components, opitonally with one or more promoter elements, that are active after reduction, in the Fischer-Tropsch synthesis. This is especially true of the products of this process comprising iron, nickel, or cobalt.

The catalysts of the process of this invention can be reduced by contact with a hydrogen-containing gas at an elevated temperature and pressure. The resulting reduced catalyst can be used in the preparation of hydrocarbons by contacting the catalyst with a mixture of carbon monoxide and hydrogen at an elevated temperature and pressure. Typically, this preparation is carried out at a temperature in the range of from about 125° C. to about 350° C., preferably from about 175° C. to about 250° C. The reaction pressure is typically in a range from about 5 bar to about 100 bar, preferably from about 12 bar to about 50 bar. The hydrogen/carbon monoxide molar ratio in the feed gas is typically greater than about 1.5, preferably between about 1.75 and about 2.25. Any unconverted hydrogen and carbon monoxide can be recycled for further contact with the catalyst. In such an arrangement, the molar ratio of hydrogen to carbon monoxide in the recycle gas actually contacting the catalyst can be considerably lower than that of the feed gas, for example, in the range of from about 0.9 to about 1.3, preferably about 1.1.

The process of the present invention is further described in the following examples which are provided for illustrative purposes only and are not to be construed as limiting the invention.

ILLUSTRATIVE EMBODIMENT

Values for the loss on ignition are quoted on the basis of water lost upon heating the sample to a temperature in the range of from about 550° C. to about 600° C. The extrusion process in the following example was conducted using a 1 inch Bonnot extruder having a 1.7 millimeter Delrin trilobe matrix dieplate insert yielding straight trilobe extrudates having a nominal diameter of 1.7 millimeters.

Extrudate Preparation

A mixture comprising zirconium hydroxide [$Zr(OH)_4$, 40% wt equivalent of $ZrO_2$, 50 g; $Zr(OH)_4$, 47% wt equivalent of $ZrO_2$, 100 g], ammonium zirconium carbonate (20% wt $ZrO_2$, 40 g) and silica (precipitated silica having an average particle size of 50 microns, surface area of 450 $m^2/g$ and a loss on ignition of 14% wt, 29 g) was mulled for a period of about 40 minutes. Two grams of a 2% wt aqueous solution of a polyelectrolyte was added and the resulting mixture was mulled for an additional 5 minutes, yielding a mixture having a loss on ignition of 53.8% and a pH of 8.4.

The resulting mixture was extruded to yield trilobe extrudates. The resulting extrudates were dried at a temperature of 120° C. and calcined at a temperature of 530° C. for 60 minutes. The resulting extrudates had a high crush strength, a pore volume ($H_2O$) of 0.257 ml/g and a surface area of 136 $m^2/g$. The extrudates comprised 75.6% wt (±7.6) zirconia and 22.7% wt (±2.3) silica.

Cobalt-Containing Catalyst Preparation

Cobalt nitrate hexahydrate [$Co(NO_3)_2.6H_2O$, 16.7 g] was melted in an oven by heating to a temperature of 84° C. to yield an aqueous solution of cobalt nitrate (10.0 ml). Extrudates (39.13 g), as prepared above, were impregnated with cobalt by immersion in the aqueous solution of cobalt nitrate at 84° C. The impregnated extrudates were dried for 30 minutes at a temperature of 60° C. Finally, the extrudates were calcined for a period of 60 minutes at 500° C.

What is claimed is:

1. A process for the preparation of a zirconia-based catalyst comprising mulling a mixture of a zirconia source and a solvent, which mixture has a solids content of from about 20% to about 60% by weight, extruding the mixture and calcining the resulting extrudates.

2. The process of claim 1 wherein the zirconia source is a zirconium salt.

3. The process of claim 1 wherein the zirconia source is zirconium hydroxide.

4. The process of claim 1 wherein the solvent is water.

5. The process of claim 1 wherein the mixture further comprises a volatile basic compound.

6. The process of claim 5 wherein the volatile basic compound is selected from the group consisting of ammonia, an ammonia-releasing compound, an ammonium compound or an organic amine.

7. The process of claim 6 wherein the basic compound is an ammonium compound.

8. The process of claim 7 wherein the ammonium compound is ammonium zirconium carbonate.

9. The process of claim 1 wherein the pH of the mixture during mulling is in the range of from about 9.0 to about 11.0.

10. The process of claim 9 wherein the pH is reduced to a value in the range of from about 7.0 to about 9.0 prior to extrusion.

11. The process of claim 10 wherein the pH is reduced by the addition of acetic acid to the mixture.

12. The process of claim 1 wherein the mixture further comprises a refractory oxide source.

13. The process of claim 12 wherein the refractory oxide source is present in an amount ranging from about 5 parts by weight to about 50 parts by weight per 100 parts by weight of zirconia present in the final product.

14. The process of claim 12 wherein the refractory oxide source is present in an amount ranging from about 5 parts by weight to about 20 parts by weight per 100 parts by weight of zirconia present in the final product.

15. The process of claim 1 wherein the mixture further comprises a surface active agent.

16. The process of claim 1 wherein the mixture further comprises a source of a catalytically active component or a source of a promoter element.

17. The process of claim 16 wherein the source is selected from Group VIII of the Periodic Table of Elements.

18. The process of claim 16 wherein the mixture comprises a source of an element selected from the group consisting of cobalt, iron or nickel.

19. The process of claim 18 wherein the mixture comprises a source of cobalt.

20. The process of claim 1 which further comprises depositing a source of a catalytically active component or a promoter element on the resulting extrudates.

21. The process of claim 20 wherein the source of the catalytically active component is selected from Group VIII of the Periodic Table of Elements.

22. The process of claim 21 wherein the catalytically active component is selected from the group consisting of cobalt, iron or nickel.

23. The process of claim 20 wherein the source of the catalytically active component is deposited by impregnation.

24. A process for the preparation of a zirconia-based catalyst comprising:
 a. mulling a mixture of a zirconia precursor, zirconium hydroxide, water, ammonium zirconium carbonate, a refractory oxide in an amount ranging from about 5 parts by weight to about 50 parts by weight per 100 parts by weight of zirconia present in the final product, and a source of cobalt, which mixture has a solids content of from about 20% to about 60% by weight and has a pH during mulling in the range from about 9.0 to about 11.0;
 b. reducing the pH of the mixture prior to extruding the mixture to a value in the range of from about 7.0 to about 9.0 by adding acetic acid;
 c. extruding the mixture to produce extrudates;
 d. calcining the resulting extrudates; and
 e. impregnating the extrudates with a source of cobalt.

25. A zirconia-based catalyst prepared by mulling a mixture of a zirconia source and a solvent, which mixture has a solids content of from about 20% by weight to about 60% by weight, extruding the mixture to produce an extrudate, calcining the extrudate; and depositing on the calcined extrudate a source of a catalytically active component selected from the group consisting of cobalt, iron or nickel.

* * * * *